United States Patent
McKay (10) Patent No.: US 8,758,791 B2
(45) Date of Patent: Jun. 24, 2014

(54) HIGHLY COMPRESSION RESISTANT MATRIX WITH POROUS SKELETON

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 267 days.

(21) Appl. No.: 12/693,469

(22) Filed: Jan. 26, 2010

(65) Prior Publication Data

US 2011/0182965 A1 Jul. 28, 2011

(51) Int. Cl.
- *A61K 9/00* (2006.01)
- *A61K 38/18* (2006.01)
- *A61K 38/39* (2006.01)

(52) U.S. Cl.
USPC .......... 424/422; 424/425; 424/426; 424/93.1; 424/93.7; 514/7.6; 514/8.8; 514/16.7; 514/17.2

(58) Field of Classification Search
None
See application file for complete search history.

(56) References Cited

U.S. PATENT DOCUMENTS

| | | |
|---|---|---|
| 4,624,255 A | 11/1986 | Schenck et al. |
| 4,776,890 A | 10/1988 | Chu |
| 4,795,467 A | 1/1989 | Piez et al. |
| 4,863,457 A | 9/1989 | Lee |
| 5,522,844 A | 6/1996 | Johnson |
| 5,776,193 A | 7/1998 | Kwan et al. |
| 5,868,789 A | 2/1999 | Huebner |
| 6,018,095 A | 1/2000 | Lerch et al. |
| 6,037,519 A | 3/2000 | McKay |
| 6,069,129 A | 5/2000 | Sandberg et al. |
| 6,179,862 B1 | 1/2001 | Sawhney |
| 6,287,588 B1 | 9/2001 | Shih et al. |
| 6,311,690 B1 | 11/2001 | Jefferies |
| 6,316,091 B1 | 11/2001 | Richart et al. |
| 6,331,311 B1 | 12/2001 | Brodbeck et al. |
| 6,428,804 B1 | 8/2002 | Suzuki et al. |
| 6,432,063 B1 | 8/2002 | Marcus |
| 6,461,631 B1 | 10/2002 | Dunn et al. |
| 6,491,651 B1 | 12/2002 | Leahy et al. |
| 6,589,549 B2 | 7/2003 | Shih et al. |
| 6,630,155 B1 | 10/2003 | Chandrashekar et al. |
| 6,632,457 B1 | 10/2003 | Sawhney |
| 6,696,073 B2 | 2/2004 | Boyce et al. |
| 6,756,058 B2 | 6/2004 | Brubaker et al. |
| 6,773,714 B2 | 8/2004 | Dunn et al. |
| 6,863,694 B1 | 3/2005 | Boyce et al. |
| 6,974,462 B2 | 12/2005 | Sater |
| 6,974,862 B2 | 12/2005 | Ringeisen et al. |
| 7,122,057 B2 | 10/2006 | Beam et al. |
| 7,144,412 B2 | 12/2006 | Wolf et al. |

(Continued)

FOREIGN PATENT DOCUMENTS

| | | |
|---|---|---|
| WO | 9639203 A1 | 12/1996 |
| WO | 03005961 A2 | 1/2003 |

OTHER PUBLICATIONS

U.S. Appl. No. 12/397,405, filed on Mar. 4, 2009.
U.S. Appl. No. 12/194,432, filed on Aug. 19, 2008.

(Continued)

*Primary Examiner* — Elizabeth C Kemmerer
(74) *Attorney, Agent, or Firm* — Sorell Lenna & Schmidt LLP (57) ABSTRACT

A highly compression resistant matrix is provided for implantation at or near a target tissue site beneath the skin. The matrix comprises a polymer and a ceramic skeleton. The compression resistance provides retention of a volume that facilitates bone regeneration.

19 Claims, 1 Drawing Sheet

(56) References Cited

U.S. PATENT DOCUMENTS

| | | |
|---|---|---|
| 7,166,570 B2 | 1/2007 | Hunter et al. |
| 7,189,263 B2 | 3/2007 | Erbe et al. |
| 7,220,281 B2 | 5/2007 | Lambrecht et al. |
| 7,229,441 B2 | 6/2007 | Trieu et al. |
| 7,235,043 B2 | 6/2007 | Gellman et al. |
| 7,318,840 B2 | 1/2008 | McKay |
| 7,329,259 B2 | 2/2008 | Cragg |
| 7,361,168 B2 | 4/2008 | Makower et al. |
| 7,367,978 B2 | 5/2008 | Drewry et al. |
| 7,371,409 B2 | 5/2008 | Petersen et al. |
| 7,449,019 B2 | 11/2008 | Uchida et al. |
| 7,462,155 B2 | 12/2008 | England |
| 7,482,174 B2 | 1/2009 | Kiefer et al. |
| 7,722,895 B1 * | 5/2010 | McKay et al. ............. 424/423 |
| 2001/0014830 A1 | 8/2001 | Kwan et al. |
| 2001/0014831 A1 | 8/2001 | Scarborough |
| 2002/0009454 A1 | 1/2002 | Boone et al. |
| 2002/0082694 A1 | 6/2002 | McKay |
| 2002/0090398 A1 | 7/2002 | Dunn et al. |
| 2003/0009235 A1 | 1/2003 | Manrique et al. |
| 2003/0133967 A1 | 7/2003 | Ruszczak et al. |
| 2003/0204191 A1 | 10/2003 | Sater et al. |
| 2004/0072799 A1 | 4/2004 | Li et al. |
| 2004/0082540 A1 | 4/2004 | Hermida Ochoa |
| 2004/0214793 A1 | 10/2004 | Hermida Ochoa |
| 2004/0249463 A1 | 12/2004 | Bindseil et al. |
| 2005/0025809 A1 | 2/2005 | Hasirci et al. |
| 2005/0043813 A1 | 2/2005 | Kusanagi et al. |
| 2005/0142163 A1 | 6/2005 | Hunter et al. |
| 2005/0186261 A1 | 8/2005 | Avelar et al. |
| 2005/0197293 A1 | 9/2005 | Mellis et al. |
| 2005/0246021 A1 | 11/2005 | Ringeisen et al. |
| 2006/0079773 A1 | 4/2006 | Mourad et al. |
| 2006/0106361 A1 | 5/2006 | Muni et al. |
| 2006/0148903 A1 | 7/2006 | Burch et al. |
| 2006/0189944 A1 | 8/2006 | Campbell et al. |
| 2006/0247772 A1 | 11/2006 | McKay |
| 2006/0270037 A1 | 11/2006 | Kato et al. |
| 2007/0156180 A1 | 7/2007 | Jaax et al. |
| 2007/0185367 A1 | 8/2007 | Abdou |
| 2007/0185497 A1 | 8/2007 | Cauthen et al. |
| 2007/0202074 A1 | 8/2007 | Shalaby |
| 2007/0243225 A1 | 10/2007 | McKay |
| 2007/0243228 A1 | 10/2007 | McKay |
| 2007/0254041 A1 * | 11/2007 | Drapeau et al. ............. 424/550 |
| 2007/0259019 A1 | 11/2007 | McKay |
| 2008/0008988 A1 | 1/2008 | McKay et al. |
| 2008/0019969 A1 | 1/2008 | Gorman |
| 2008/0019970 A1 | 1/2008 | Gorman |
| 2008/0019975 A1 | 1/2008 | Gorman |
| 2008/0065228 A1 | 3/2008 | Kim |
| 2008/0091207 A1 | 4/2008 | Truckai et al. |
| 2008/0147197 A1 | 6/2008 | McKay |
| 2008/0152687 A1 | 6/2008 | Thorne |
| 2008/0175911 A1 | 7/2008 | McKay et al. |
| 2008/0187571 A1 | 8/2008 | Clineff et al. |
| 2008/0213283 A1 | 9/2008 | Olmarker et al. |
| 2008/0294261 A1 | 11/2008 | Pauza et al. |
| 2008/0317805 A1 | 12/2008 | McKay et al. |
| 2009/0012625 A1 | 1/2009 | Ying et al. |
| 2009/0024135 A1 | 1/2009 | Triplett et al. |
| 2009/0280179 A1 | 11/2009 | Neumann et al. |

OTHER PUBLICATIONS

U.S. Appl. No. 12/193,794, filed on Aug. 19, 2008.
International Search Report PCT/US2011/022582 the counterpart application mailed on Oct. 27, 2011.
Yoshitake Takahashi et al., Biomaterials 2005, vol. 26, pp. 4856-4865 See abstract: p. 4857; p. 4858, Table 1.
Brian Kwon, The Spine Journal 2005, vol. 5, pp. 224S-230S See p. 226S.
N. Passuti et al., Eur J. Orthop Surg Traumatol 1997, vol. 7., pp. 79-84 See abstract.

* cited by examiner

HIGHLY COMPRESSION RESISTANT MATRIX WITH POROUS SKELETON

BACKGROUND

Bone is a composite material that is composed of impure hydroxyapatite, collagen and a variety of non-collagenous proteins, as well as embedded and adherent cells. Due to disease, a congenital defect or an accident, a person may lose or be missing part or all of one or more bones or regions of cartilage in his or her body, and/or have improper growth or formation of bone and/or cartilage.

Mammalian bone tissue is known to contain one or more proteinaceous materials that are active during growth and natural bone healing. These materials can induce a developmental cascade of cellular events that results in bone formation. Typically, the developmental cascade of bone formation involves chemotaxis of mesenchymal cells, proliferation of progenitor cells, differentiation of cartilage, vascular invasion, bone formation, remodeling and marrow differentiation.

When bone is damaged, often bone grafting procedures are performed to repair the damaged bone, especially in cases where the damage is complex, poses a significant risk to the patient, and/or fails to heal properly. Bone grafting is also used to help fusion between vertebrae, correct deformities, or provide structural support for fractures of the spine. In addition to fracture repair, bone grafting is also used to repair defects in bone caused by birth defects, traumatic injury, or surgery for bone cancer.

Some grafting procedures utilize a variety of natural and synthetic matrixes with or instead of bone (e.g., collagen, silicone, acrylics, hydroxyapatite, calcium sulfate, ceramics, etc.). To place the matrix at the bone defect, the surgeon makes an incision in the skin over the bone defect and shapes the matrix to fit into the defect. As persons of ordinary skill are aware, growth factors (e.g., bone morphogenic protein-2) may be placed on the matrix in order to spur the patient's body to begin the formation of new bone and/or cartilage. These growth factors act much like a catalyst, encouraging the necessary cells (including, but not limited to, mesenchymal stem cells, osteoblasts, and osteoclasts) to more rapidly migrate into the matrix, which is eventually resorbed via a cell-mediated process, and newly formed bone is deposited at or near the bone defect. In this manner severe fractures may be healed, and vertebrae successfully fused.

Unfortunately, currently known matrices often contain essentially spherical or rounded particles that do not provide sufficient compression resistance for some tissue engineering applications. Thus, there is a need to develop improved matrices that have desirable resistance properties.

SUMMARY

Compositions and methods are provided that improve anatomical tissue regeneration. These compositions are compression resistant matrices that contain a porous ceramic skeleton. Through the use of the porous ceramic skeleton, which may be embedded in the matrix, the composition has more compression resistance than commonly used matrices. These compositions also have improved shape retention, which renders them more desirable for tissue regeneration, and facilitates the formation of the generation of adequate volumes of newly formed bone.

The compression resistance is imparted because the ceramic skeleton is able to carry with it any loads placed on the matrix from the surrounding muscles or external forces. Compression resistance is needed for many tissue engineering applications such as for example, tibial plateau fractures, acetabuler defects, long bone comminuted fractures, oral maxillofacial defects, spinal fusions and cartilage subchondral defects.

In some embodiments, a compression resistant matrix is provided for implantation at or near a target tissue site beneath the skin, the matrix comprising a porous ceramic skeleton and a polymer.

In some embodiments, a compression resistant matrix for implantation is provided such that it may be implanted at or near a target tissue site beneath the skin. The matrix comprises a porous ceramic skeleton disposed throughout the matrix in its interior and a polymer disposed throughout the matrix in its interior and extending to its exterior such that the matrix is porous and compression resistant, wherein said matrix is not compressed any more than about 10% in any one direction for a period of at least about 30 days in vivo or at least about 60 days in vivo.

The compression resistant matrix may be designed such that under the normal stress of both stationary loads and loads that change with movement, it does not change in size or shape, or is compressed no more than about 20% in any one direction, no more than about 18% in any one direction, no more than about 16% in any one direction, no more than about 14% in any one direction, no more than about 12% in any one direction, no more than about 10% in any one direction, no more than about 8% in any one direction, no more than about 6% in any one direction, no more than about 4% in any one direction, or no more than about 2% in any one direction.

In some embodiments, the aforementioned degree of compression resistance is maintained for a period of at least about 30 days, at least about 40 days, at least about 50 days, at least about 60 days, at least about 75 days, at least about 90 days, at least about 120 days, at least about 150 days or at least about 180 days in vivo.

In some embodiments, a method is provided for making a matrix for implantation, wherein said method comprises the steps of combining a porous ceramic skeleton with a polymer slurry that is comprised of a polymer.

Examples of uses of the matrix include but are not limited to correcting large oral maxillofacial defects, building up alveolar and mandible ridge heights for future dental implant placement, addressing cranial defects, addressing long bone segmental defects and performing posterolateral spine fusions.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values are as precise as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Additionally, unless defined otherwise or apparent from context, all technical and scientific terms used herein have the same meanings as commonly understood by one of ordinary skill in the art to which this invention belongs.

Unless explicitly stated or apparent from context, the following terms or phrases have the definitions provided below:

DEFINITIONS

It is noted that, as used in this specification and the appended claims, the singular forms "a," "an," and "the," include plural referents unless expressly and unequivocally limited to one referent. Thus, for example, reference to "a matrix" includes one, two, three or more matrices.

The term "biodegradable" includes that all or parts of the matrix will degrade over time by the action of enzymes, by hydrolytic action and/or by other similar mechanisms in the human body. In various embodiments, "biodegradable" includes that a matrix can break down or degrade within the body to non-toxic components. By "bioerodible" it is meant that the matrix will erode or degrade over time due, at least in part, to contact with substances found in the surrounding tissue, fluids or by cellular action. By "bioabsorbable" or "bioresorbable" it is meant that the matrix will be broken down and absorbed within the human body, for example, by a cell or tissue. "Biocompatible" means that the matrix will not cause substantial tissue irritation or necrosis at the target tissue site.

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug.

The term "mammal" refers to organisms from the taxonomy class "mammalian," including but not limited to humans, other primates such as chimpanzees, apes, orangutans and monkeys, rats, mice, cats, dogs, cows, horses, etc.

The "matrix" of the present application is utilized as a scaffold for bone and/or cartilage repair, regeneration, and/or augmentation. Typically, the matrix provides a 3-D matrix of interconnecting pores that act as a pliant scaffold for cell migration. The morphology of the matrix guides cell migration and cells are able to migrate into or over the matrix, respectively. The cells then are able to proliferate and synthesize new tissue and form bone and/or cartilage.

The term "porous" refers to a framework having interconnecting struts that define a plurality of interstices.

The phrases "sustained release" and "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the drug bead, foam and/or component thereof, or as the result of metabolic transformation or dissolution of the therapeutic agent(s) or conjugates of therapeutic agent(s).

The term "target tissue site" is intended to mean the location of the tissue to be treated. Typically the placement site of the matrix will be the same as the target site to provide a scaffolding for bone growth. However, the present application also contemplates positioning the matrix at a placement site at or near the target site such that when a therapeutic agent is present, the therapeutic agent can be delivered to the surrounding vasculature, which carries the agent to the desired nearby target site. As used herein, the term "at or near" includes embodiments where the placement site and target site are within close proximity.

A "therapeutically effective amount" or "effective amount" is such that when administered, a drug results in alteration of the biological activity, such as, for example, promotion of bone, cartilage and/or other tissue (e.g., vascular tissue) growth, inhibition of inflammation, reduction or alleviation of pain, improvement in the condition through inhibition of an immunologic response, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments the formulation is designed for immediate release. In other embodiments the formulation is designed for sustained release. In other embodiments, the formulation comprises one or more immediate release surfaces and one or more sustained release surfaces. In some embodiments, the matrix comprises an effective amount of a growth factor.

The terms "treating" and "treatment" when used in connection with a disease or condition refer to executing a protocol that may include osteochondral repair procedure, administering one or more drugs to a patient (human or other mammal), in an effort to alleviate signs or symptoms of the disease or condition or immunological response. Alleviation can occur prior to signs or symptoms of the disease or condition appearing, as well as after their appearance. Thus, treating or treatment includes preventing or prevention of disease or undesirable condition. In addition, treating, treatment, preventing or prevention do not require complete alleviation of signs or symptoms, does not require a cure, and specifically includes protocols that have only a marginal effect on the patient. In some embodiments, the matrix can be used to treat subchondral, osteochondral, hyaline cartilage and/or condyle defects.

Reference will now be made in detail to certain embodiments of the invention. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

In some embodiments, there is a matrix for implantation at or near a target tissue site beneath the skin, the matrix comprising a porous ceramic skeleton and a polymer.

Ceramic Skeleton

The ceramic skeleton may contain a calcium phosphate ceramic material, such as dicalcium phosphate, tricalcium phosphate, amorphous hydroxyapatite, crystalline hydroxyapatite, coralline hydroxyapatite, hydroxyapatite e.g., ETEX CaP, silicate containing ceramics or a combination thereof. In some embodiments the ceramic material consists of essentially or comprises fast resorbing $CaPO_4$. It may also be possible to include some polymer (e.g., natural or synthetic degradable polymer) in the ceramic slurry to give the skeleton a degree of ductility and to render it less brittle.

The porous ceramic can be fabricated by pouring the ceramic slurry into a porous mold made out of a material that can be dissolved away or burned out after the ceramic has set. The porous skeleton can also be sintered at high temperatures, e.g., at temperatures between about 900 and about 1700 degrees C. In some embodiments the skeleton is sintered between about 900 degrees and about 1100 degrees C. or between about 1100 and about 1300 degrees C. or between about 1300 and about 1500 degrees C. or between about 1500 degrees and about 1700 degrees C. Examples of parameters that may be useful in some embodiments and under which to form a ceramic are those provided in U.S. Pat. No. 6,316,091, to Richart et al., the disclosure of which is incorporated by reference as if set forth fully herein.

In some embodiments, the mold enables the creation of a ceramic with about 50% to about 90% porosity or about 50% to about 80% porosity, or about 60% to about 80% porosity.

Polymer

The polymer may for example be collagen. The collagen may facilitate cellular migration and attachment during tissue regeneration. In some embodiments, the matrix comprises collagen. Examples of collagens include human or non-human (bovine, ovine, and/or porcine), as well as recombinant collagen or combinations thereof. Examples of suitable collagen include, but are not limited to, human collagen type I, human collagen type II, human collagen type III, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collagen type XXI, human collagen type XXII, human collagen type XXIII, human collagen type XXIV, human collagen type XXV, human collagen type XXVI, human collagen type XXVII, and human collagen type XXVIII, or combinations thereof. Collagen further may comprise hetero- and homo-trimers of any of the above-recited collagen types. In some embodiments, the collagen comprises hetero- or homo-trimers of human collagen type I, human collagen type II, human collagen type III, or combinations thereof.

In some embodiments, the matrix comprises collagen-containing biomaterials from the implant market which, when placed in a bone defect, provide scaffolding around which the patient's new bone will grow, gradually replacing the carrier matrix as the target site heals. Examples of suitable carrier matrices may include, but are not limited to, the MasterGraft® Matrix produced by Medtronic Sofamor Danek, Inc., Memphis, Tenn.; MasterGraft® Putty produced by Medtronic Sofamor Danek, Inc., Memphis, Tenn.; Absorbable Collagen Sponge ("ACS") produced by Integra LifeSciences Corporation, Plainsboro, N.J.; bovine skin collagen fibers coated with hydroxyapatite, e.g. Healos®. marketed by Johnson & Johnson, USA; collagen sponges, e.g. Hemostagene® marketed by Coletica S A, France, or e.g. Helisat® marketed by Integra Life Sciences Inc., USA; and Collagraft® Bone Graft Matrix produced by Zimmer Holdings, Inc., Warsaw, Ind.

In particular, collagen cross-linking is achieved by laccase-induced peptide cross-linking and suitable bridging molecules.

Cross-linking reaction preferably occurs at pH value of 5 to 7. The reaction may be allowed to proceed within the temperature range of 2 to 80 degrees centigrade or within the range of 20 to 37 degrees centigrade, or within the range of 25 to 30 degrees centigrade.

In some embodiments, there is a method for making a composition for implantation. In this method one combines a porous ceramic skeleton with a polymer slurry that is comprised of a polymer.

After the porous skeleton is made, a polymer slurry such as collagen is poured into the highly porous ceramic skeleton, freeze dried, and possibly chemically crosslinked, resulting in a porous collagen structure within the large pores on the ceramic skeleton. The collagen is important to allow for cellular migration and attachment during tissue regeneration.

In some embodiments, one may treat the matrix to cross-link the polymer. Methods for cross-linking polymers are well-known to persons of ordinary skill in the art. Examples of the polymer also include but are not limited to keratin, chitosan, and other natural or synthetic degradable polymers or combinations thereof.

Matrix

The matrix, which comprises the polymer and the ceramic skeleton provides a tissue scaffold for the cells to guide the process of tissue formation in vivo in three dimensions. The ceramic skeleton may be disposed continuously throughout the interior of the matrix, and it may be covered with the polymer such that the outside surfaces of the matrix comprises the polymer. In some embodiments, the outside surface is 0.01 to 1 mm thick.

The morphology of the matrix guides cell migration and cells are able to migrate into or over the scaffold. The cells then are able to proliferate and synthesize new tissue and form bone and/or cartilage. In some embodiments, one or more tissue matrices are stacked on one another.

In some embodiments, the matrix comprises a plurality of pores. Unless otherwise specified, these and other pore sizes refer to the size of the pores after the polymer has been added and cross-linked if cross-linking has occurred. The ceramic skeleton pores may be in the range of about 1 to about 10 mm in diameter, or about 4 to about 6 mm in diameter, e.g., about 5 mm and have a total porosity of about 50-90% or about 60-80%, e.g., about 70%. The collagen matrix inside the ceramic skeleton may have pores in the range of 0.01-1 mm diameter or 0.03-0.08 mm in diameter, e.g., about 0.05 mm and have a porosity of about 80-99% or about 93-97%, e.g., about 95%. In some embodiments all of the pores are within the aforementioned size ranges. In some embodiments, substantially all (e.g., at least 80% or at least 90%) of the pores are within the aforementioned size ranges.

In some embodiments, the matrix has a porosity of at least about 30%, at least about 50%, at least about 60%, at least about 70%, at least about 90%. The pores may support ingrowth of cells, formation or remodeling of bone, cartilage and/or vascular tissue.

Due to their very macroporosity as such, the implantable biocompatible porous solid matrices such as ceramics, and more specifically the matrices having interconnected pores, are advantageous in that they increase the interchange surface area with the biological medium, are bioresorbable, promote the revascularization of the tissues and have excellent osteoconductive properties. Moreover, growth agents may be deposited into the pores by means of precipitation. In some embodiments, the matrix has compression strength of at least about 5 MPa, at least about 10 MPa, at least about 20 MPa, at least about 30 MPa, or at least about 40 MPa.

In some embodiments, there may be about 0.2-2% collagen and about 98-99.8% ceramic, wherein the percentages are based on weight.

The matrix may comprise additional natural and/or synthetic material. For example, the tissue scaffold may comprise poly (alpha-hydroxy acids), poly (lactide-co-glycolide) (PLGA), polylactide (PLA), polyglycolide (PG), polyethylene glycol (PEG) conjugates of poly (alpha-hydroxy acids), polyorthoesters (POE), polyaspirins, polyphosphagenes, collagen, hydrolyzed collagen, gelatin, hydrolyzed gelatin, fractions of hydrolyzed gelatin, elastin, starch, pre-gelatinized starch, hyaluronic acid, chitosan, keratin, alginate, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate), polydioxanone, methylmethacrylate (MMA), MMA and N-vinylpyyrolidone, polyamide, oxycellulose, copolymer of glycolic acid and trimethylene carbonate, polyesteramides, polyetheretherketone, polymethylmethacrylate, silicone, hyaluronic acid, chitosan, or combinations thereof.

In some embodiments, the matrix may comprise a resorbable ceramic (e.g., hydroxyapatite, tricalcium phosphate, bioglasses, calcium sulfate, etc.) tyrosine-derived polycarbonate poly (DTE-co-DT carbonate), in which the pendant group via the tyrosine—an amino acid—is either an ethyl ester (DTE) or free carboxylate (DT) or combinations thereof.

In some embodiments, the embodiments the matrix may comprise particles of bone-derived materials. The bone-derived material may include one or more of non-demineralized bone particles, demineralized bone particles, lightly demineralized bone particles, and/or deorganified bone particles.

In some embodiments, the matrix may be seeded with harvested bone cells and/or bone tissue, such as for example, cortical bone, autogenous bone, allogenic bones and/or xenogenic bone. In some embodiments, the matrix may be seeded with harvested cartilage cells and/or cartilage tissue (e.g., autogenous, allogenic, and/or xenogenic cartilage tissue). For example, before insertion into the target tissue site, the matrix can be wetted with the graft bone tissue/cells, usually with bone tissue/cells aspirated from the patient, at a ratio of about 3:1, 2:1, 1:1, 1:2 or 1:3 by volume. The bone tissue/cells are permitted to soak into the matrix provided, and the matrix may be kneaded by hand or machine, thereby obtaining a pliable consistency that may subsequently be packed into the bone defect. In some embodiments, the matrix provides a malleable, non-water soluble carrier that permits accurate placement and retention at the implantation site.

Additionally, in some embodiments the matrix may contain an inorganic material, such as an inorganic ceramic and/or bone substitute material. Examples of inorganic materials or bone substitute materials include but are not limited to aragonite, dahlite, calcite, amorphous calcium carbonate, vaterite, weddellite, whewellite, struvite, urate, ferrihydrate, francolite, monohydrocalcite, magnetite, goethite, dentin, calcium carbonate, calcium sulfate, calcium phosphosilicate, sodium phosphate, calcium aluminate, calcium phosphate, hydroxyapatite, alpha-tricalcium phosphate, dicalcium phosphate, β-tricalcium phosphate, tetracalcium phosphate, amorphous calcium phosphate, octacalcium phosphate, BIOGLASS™, fluoroapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium sodium, potassium, etc.), or combinations or derivatives thereof.

In some embodiments, tissue will infiltrate the matrix to a degree of about at least 25 percent within about 1 month to about 6 months after implantation of the matrix. In some embodiments, about 75 percent of the matrix will be infiltrated by tissue within about 2-3 months after implantation of the matrix. In some embodiments, the matrix will be substantially, e.g., about 90 percent or more, submerged in or enveloped by tissue within about 6 months after implantation of the matrix. In some embodiments, the matrix will be completely submerged in or enveloped by tissue within about 9-12 months after implantation.

In some embodiments, the matrix has a thickness of from about 2 mm to 40 mm, or from about 4 mm to 20 mm, or about 5 mm to 10 mm. Clearly, different bone defects (e.g., osteochondral defects) may require different matrix thicknesses.

In some embodiments, the matrix has a density of between about 1.6 g/cm$^3$, and about 0.05 g/cm$^3$. In some embodiments, the matrix has a density of between about 1.1 g/cm$^3$, and about 0.07 g/cm$^3$. For example, the density may be less than about 1 g/cm$^3$, less than about 0.7 g/cm$^3$, less than about 0.6 g/cm$^3$, less than about 0.5 g/cm$^3$, less than about 0.4 g/cm$^3$, less than about 0.3 g/cm$^3$, less than about 0.2 g/cm$^3$, or less than about 0.1 g/cm$^3$.

The shape of the matrix may be tailored to the site at which it is to be situated. For example, it may be in the shape of a morsel, a plug, a pin, a peg, a cylinder, a block, a wedge, a sheet, etc.

In some embodiments, the diameter or diagonal of the matrix can range from 1 mm to 50 mm. In some embodiments, the diameter or diagonal of the matrix can range from 1 mm to 30 mm, or 5 mm to 10 mm which is small enough to fit through an endoscopic cannula, but large enough to minimize the number of matrices needed to fill a large the bone defect (e.g., osteochondral defect).

In some embodiments, the matrix may be made by injection molding, compression molding, blow molding, thermoforming, die pressing, slip casting, electrochemical machining, laser cutting, water-jet machining, electrophoretic deposition, powder injection molding, sand casting, shell mold casting, lost tissue scaffold casting, plaster-mold casting, ceramic-mold casting, investment casting, vacuum casting, permanent-mold casting, slush casting, pressure casting, die casting, centrifugal casting, squeeze casting, rolling, forging, swaging, extrusion, shearing, spinning, powder metallurgy compaction or combinations thereof.

In some embodiments, a therapeutic agent (including one or more growth factors) may be disposed on or in the matrix by hand, electrospraying, ionization spraying or impregnating, vibratory dispersion (including sonication), nozzle spraying, compressed-air-assisted spraying, brushing and/or pouring. For example, a growth factor such as rhBMP-2 may be disposed on or in the matrix.

In some embodiments, the matrix may comprise sterile and/or preservative free material.

The matrix can be implanted by hand or machine in procedures such as for example, laparoscopic, arthroscopic, neuroendoscopic, endoscopic, rectoscopic procedures or the like.

In some embodiments, the matrix can upon implant withstand a pressure in the range of 2-40 MPa or 5-20 MPa, and last for a duration of about 3-9 months.

Growth Factors

In some embodiments, a growth factor and/or therapeutic agent may be disposed on or in the matrix by hand, electrospraying, ionization spraying or impregnating, vibratory dispersion (including sonication), nozzle spraying, compressed-air-assisted spraying, brushing and/or pouring. For example, a growth factor such as rhBMP-2 may be disposed on or in the biodegradable carrier by the surgeon before the biodegradable matrix is administered or it may be available from the manufacturer beforehand.

The biodegradable matrix may be biodegradable and comprise at least one growth factor. Examples of these growth factors include osteoinductive agents (e.g., agents that cause new bone growth in an area where there was none) and/or osteoconductive agents (e.g., agents that cause ingrowth of cells into and/or through the matrix). Osteoinductive agents can be polypeptides or polynucleotides compositions. Polynucleotide compositions of the osteoinductive agents include, but are not limited to, isolated Bone Morphogenic Protein (BMP), Vascular Endothelial Growth Factor (VEGF), Connective Tissue Growth Factor (CTGF), Osteoprotegerin, Growth Differentiation Factors (GDFs), Cartilage Derived Morphogenic Proteins (CDMPs), Lim Mineralization Proteins (LMPs), Platelet derived growth factor, (PDGF or rhPDGF), Insulin-like growth factor (IGF) or Transforming Growth Factor beta (TGF-beta) polynucleotides. Polynucleotide compositions of the osteoinductive agents include, but are not limited to, gene therapy vectors harboring polynucleotides encoding the osteoinductive polypeptide of interest. Gene therapy methods often utilize a polynucleotide, which codes for the osteoinductive polypeptide operatively linked or associated to a promoter or any other genetic elements necessary for the expression of the osteoinductive polypeptide by the target tissue. Such gene therapy and delivery techniques are known in the art (see, for example, International Publication No. WO90/11092, the disclosure of which is herein incorporated by reference in its entirety). Suitable gene therapy vectors include, but are not limited to, gene therapy vectors that do not integrate into the host genome. Alternatively, suitable gene therapy vectors include, but are not limited to, gene therapy vectors that integrate into the host genome.

In some embodiments, the polynucleotide is delivered in plasmid formulations. Plasmid DNA or RNA formulations refer to polynucleotide sequences encoding osteoinductive polypeptides that are free from any delivery vehicle that acts to assist, promote or facilitate entry into the cell, including viral sequences, viral particles, liposome formulations, lipofectin, precipitating agents or the like. Optionally, gene therapy compositions can be delivered in liposome formulations and lipofectin formulations, which can be prepared by methods well known to those skilled in the art. General methods are described, for example, in U.S. Pat. Nos. 5,593,972, 5,589,466, and 5,580,859, the disclosures of which are herein incorporated by reference in their entireties.

Gene therapy vectors further comprise suitable adenoviral vectors including, but not limited to for example, those described in U.S. Pat. No. 5,652,224, which is herein incorporated by reference.

Polypeptide compositions of the isolated osteoinductive agents include, but are not limited to, isolated Bone Morphogenic Protein (BMP), Vascular Endothelial Growth Factor (VEGF), Connective Tissue Growth Factor (CTGF), Osteoprotegerin, Growth Differentiation Factors (GDFs), Cartilage Derived Morphogenic Proteins (CDMPs), Lim Mineralization Proteins (LMPs), Platelet derived growth factor, (PDGF or rhPDGF), Insulin-like growth factor (IGF) or Transforming Growth Factor beta (TGF-beta707) polypeptides. Polypeptide compositions of the osteoinductive agents include, but are not limited to, full length proteins, fragments or variants thereof.

Variants of the isolated osteoinductive agents include, but are not limited to, polypeptide variants that are designed to increase the duration of activity of the osteoinductive agent in vivo. Typically, variant osteoinductive agents include, but are not limited to, full length proteins or fragments thereof that are conjugated to polyethylene glycol (PEG) moieties to increase their half-life in vivo (also known as pegylation). Methods of pegylating polypeptides are well known in the art (See, e.g., U.S. Pat. No. 6,552,170 and European Pat. No. 0,401,384 as examples of methods of generating pegylated polypeptides). In some embodiments, the isolated osteoinductive agent(s) are provided as fusion proteins. In one embodiment, the osteoinductive agent(s) are available as fusion proteins with the Fc portion of human IgG. In another embodiment, the osteoinductive agent(s) are available as hetero- or homodimers or multimers. Examples of some fusion proteins include, but are not limited to, ligand fusions between mature osteoinductive polypeptides and the Fc portion of human Immunoglobulin G (IgG). Methods of making fusion proteins and constructs encoding the same are well known in the art.

Isolated osteoinductive agents that are included within a matrix are typically sterile. In a non-limiting method, sterility is readily accomplished for example by filtration through sterile filtration membranes (e.g., 0.2 micron membranes or filters). In one embodiment, the isolated osteoinductive agents include one or more members of the family of Bone Morphogenic Proteins ("BMPs"). BMPs are a class of proteins thought to have osteoinductive or growth-promoting activities on endogenous bone tissue, or function as procollagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

In another embodiment, isolated osteoinductive agents include osteoclastogenesis inhibitors to inhibit bone resorption of the bone tissue surrounding the site of implantation by osteoclasts. Osteoclast and osteoclastogenesis inhibitors include, but are not limited to, osteoprotegerin polynucleotides or polypeptides, as well as mature osteoprotegerin proteins, polypeptides or polynucleotides encoding the same. Osteoprotegerin is a member of the TNF-receptor superfamily and is an osteoblast-secreted decoy receptor that functions as a negative regulator of bone resorption. This protein specifically binds to its ligand, osteoprotegerin ligand (TNFSF11/OPGL), both of which are key extracellular regulators of osteoclast development.

Osteoclastogenesis inhibitors further include, but are not limited to, chemical compounds such as bisphosphonate, 5-lipoxygenase inhibitors such as those described in U.S. Pat. Nos. 5,534,524 and 6,455,541 (the contents of which are herein incorporated by reference in their entireties), heterocyclic compounds such as those described in U.S. Pat. No. 5,658,935 (herein incorporated by reference in its entirety), 2,4-dioxoimidazolidine and imidazolidine derivative compounds such as those described in U.S. Pat. Nos. 5,397,796 and 5,554,594 (the contents of which are herein incorporated by reference in their entireties), sulfonamide derivatives such as those described in U.S. Pat. No. 6,313,119 (herein incorporated by reference in its entirety), or acylguanidine compounds such as those described in U.S. Pat. No. 6,492,356 (herein incorporated by reference in its entirety).

In another embodiment, isolated osteoinductive agents include one or more members of the family of Connective Tissue Growth Factors ("CTGFs"). CTGFs are a class of proteins thought to have growth-promoting activities on connective tissues. Known members of the CTGF family include, but are not limited to, CTGF-1, CTGF-2, CTGF-4 polynucleotides or polypeptides thereof, as well as mature proteins, polypeptides or polynucleotides encoding the same.

In another embodiment, isolated osteoinductive agents include one or more members of the family of Vascular Endothelial Growth Factors ("VEGFs"). VEGFs are a class of proteins thought to have growth-promoting activities on vascular tissues. Known members of the VEGF family include, but are not limited to, VEGF-A, VEGF-B, VEGF-C, VEGF-D, VEGF-E or polynucleotides or polypeptides thereof, as well as mature VEGF-A, proteins, polypeptides or polynucleotides encoding the same.

In another embodiment, isolated osteoinductive agents include one or more members of the family of Transforming Growth Factor-beta ("TGFbetas"). TGF-betas are a class of proteins thought to have growth-promoting activities on a range of tissues, including connective tissues. Known members of the TGF-beta family include, but are not limited to, TGF-beta-1, TGF-beta-2, TGF-beta-3, polynucleotides or polypeptides thereof, as well as mature protein, polypeptides or polynucleotides encoding the same.

In another embodiment, isolated osteoinductive agents include one or more Growth Differentiation Factors ("GDFs"). Known GDFs include, but are not limited to, GDF-1, GDF-2, GDF-3, GDF-7, GDF-10, GDF-11, and GDF-15. For example, GDFs useful as isolated osteoinductive agents include, but are not limited to, the following GDFs: GDF-1 polynucleotides or polypeptides corresponding to GenBank Accession Numbers M62302, AAA58501, and AAB94786, as well as mature GDF-1 polypeptides or polynucleotides encoding the same. GDF-2 polynucleotides or polypeptides corresponding to GenBank Accession Numbers BC069643, BC074921, Q9UK05, AAH69643, or AAH74921, as well as mature GDF-2 polypeptides or polynucleotides encoding the same; GDF-3 polynucleotides or polypeptides corresponding to GenBank Accession Numbers AF263538, BC030959, AAF91389, AAQ89234, or Q9NR23, as well as mature GDF-3 polypeptides or polynucleotides encoding the same; GDF-7 polynucleotides or polypeptides corresponding to GenBank Accession Numbers AB158468, AF522369, AAP97720, or Q7Z4P5, as well as mature GDF-7 polypeptides or polynucleotides encoding the same; GDF-10 polynucleotides or polypeptides corresponding to GenBank Accession Numbers BC028237 or AAH28237, as well as mature GDF-10 polypeptides or polynucleotides encoding the same; GDF-11 polynucleotides or polypeptides corresponding to GenBank Accession Numbers AF100907, NP_005802 or 095390, as well as mature GDF-11 polypeptides or polynucleotides encoding the same; and GDF-15 polynucleotides or polypeptides corresponding to GenBank Accession Numbers BC008962, BC000529, AAH00529, or NP_004855, as well as mature GDF-15 polypeptides or polynucleotides encoding the same.

In another embodiment, isolated osteoinductive agents include Cartilage Derived Morphogenic Protein (CDMP) and Lim Mineralization Protein (LMP) polynucleotides or polypeptides. Known CDMPs and LMPs include, but are not limited to, CDMP-1, CDMP-2, LMP-1, LMP-2, or LMP-3.

CDMPs and LMPs useful as isolated osteoinductive agents include, but are not limited to, the following CDMPs and LMPs: CDMP-1 polynucleotides and polypeptides corresponding to GenBank Accession Numbers NM_000557, U13660, NP_000548 or P43026, as well as mature CDMP-1 polypeptides or polynucleotides encoding the same. CDMP-2 polypeptides corresponding to GenBank Accession Numbers or P55106, as well as mature CDMP-2 polypeptides. LMP-1 polynucleotides or polypeptides corresponding to GenBank Accession Numbers AF345904 or AAK30567, as well as mature LMP-1 polypeptides or polynucleotides encoding the same. LMP-2 polynucleotides or polypeptides corresponding to GenBank Accession Numbers AF345905 or AAK30568, as well as mature LMP-2 polypeptides or polynucleotides encoding the same. LMP-3 polynucleotides or polypeptides corresponding to GenBank Accession Numbers AF345906 or AAK30569, as well as mature LMP-3 polypeptides or polynucleotides encoding the same.

In another embodiment, isolated osteoinductive agents include one or more members of any one of the families of Bone Morphogenic Proteins (BMPs), Connective Tissue Growth Factors (CTGFs), Vascular Endothelial Growth Factors (VEGFs), Osteoprotegerin or any of the other osteoclastogenesis inhibitors, Growth Differentiation Factors (GDFs), Cartilage Derived Morphogenic Proteins (CDMPs), Lim Mineralization Proteins (LMPs), or Transforming Growth Factor-betas (TGF-betas), as well as mixtures or combinations thereof.

In another embodiment, the one or more isolated osteoinductive agents useful in the bioactive formulation are selected from the group consisting of BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18, or any combination thereof; CTGF-1, CTGF-2, CGTF-3, CTGF-4, or any combination thereof; VEGF-A, VEGF-B, VEGF-C, VEGF-D, VEGF-E, or any combination thereof; GDF-1, GDF-2, GDF-3, GDF-7, GDF-10, GDF-11, GDF-15, or any combination thereof; CDMP-1, CDMP-2, LMP-1, LMP-2, LMP-3, and/or any combination thereof; Osteoprotegerin; TGF-beta-1, TGF-beta-2, TGF-beta-3, or any combination thereof; or any combination of one or more members of these groups.

In some embodiments, BMP-7 and/or GDF-5 may be used at 1-2 mg/cc of matrix.

The concentrations of growth factor can be varied based on the desired length or degree of osteogenic effects desired.

Similarly, one of skill in the art will understand that the duration of sustained release of the growth factor can be modified by the manipulation of the compositions comprising the sustained release formulation, such as for example, modifying the percent of polymers found within a sustained release formulation, microencapsulation of the formulation within polymers, including polymers having varying degradation times and characteristics, and layering the formulation in varying thicknesses in one or more degradable polymers. These sustained release formulations can therefore be designed to provide customized time release of growth factors that stimulate the natural healing process.

The growth factor may contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfate, sodium bisulfite, sodium thiosulfate, thimerosal, methylparaben, polyvinyl alcohol and phenylethyl alcohol; solubility adjusting agents; stabilizers; and/or cohesion modifiers. In some embodiments, the growth factor may comprise sterile and/or preservative free material.

These above inactive ingredients may have multi-functional purposes including the carrying, stabilizing and controlling the release of the growth factor and/or other therapeutic agent(s). The sustained release process, for example, may be by a solution-diffusion mechanism or it may be governed by an erosion-sustained process.

In some embodiments, a pharmaceutically acceptable formulation comprising a growth factor is provided, wherein the formulation is a freeze-dried or lyophilized formulation. Typically, in the freeze-dried or lyophilized formulation an effective amount of a growth factor is provided. Lyophilized formulations can be reconstituted into solutions, suspensions, emulsions, or any other suitable form for administration or use. Lyophilized formulations are typically first prepared as liquids, then frozen and lyophilized. The total liquid volume before lyophilization can be less, equal to, or more than, the final reconstituted volume of the lyophilized formulation. The lyophilization process is well known to those of ordinary skill in the art, and typically includes sublimation of water from a frozen formulation under controlled conditions.

Lyophilized formulations can be stored at a wide range of temperatures. Lyophilized formulations may be stored at or below 30° C., for example, refrigerated at 4° C., or at room temperature (e.g., approximately 25° C.).

Lyophilized formulations of the growth factor are typically reconstituted for use by addition of an aqueous solution to dissolve the lyophilized formulation. A wide variety of aqueous solutions can be used to reconstitute a lyophilized formulation. In some embodiments, lyophilized formulations are reconstituted using water. In some embodiments, lyophilized formulations can be reconstituted with a solution containing water (e.g., USP WFI, or water for injection) or bacteriostatic water (e.g., USP WFI with 0.9% benzyl alcohol). However, solutions comprising buffers and/or excipients and/or one or more pharmaceutically acceptable carries can also be used. In some embodiments, the solutions do not contain any preservatives (e.g., are preservative free).

In some embodiments, the lyophilized growth factor (e.g., BMP) can be disposed in a vial by the manufacturer and then the surgeon can mix the diluent with the lyophilized growth factor. This mixture can then be parenterally administered to the target tissue site. The term "parenteral" as used herein refers to modes of administration which bypass the gastrointestinal tract, and include for example, intramuscular, intraperitoneal, intrasternal, subcutaneous, intra-operatively, intrathecally, intradiskally, peridiskally, epidurally, perispinally, intraarticular or combinations thereof.

The amount of growth factor, e.g., bone morphogenic protein may be sufficient to cause bone and/or cartilage growth. In some embodiments, the growth factor is rhBMP-2 and is contained in one or more matrices in an amount of from 1 to 2 mg per cubic centimeter of the biodegradable matrix. In some embodiments, the amount of rhBMP-2 morphogenic protein is from 2.0 to 2.5 mg per cubic centimeter (cc) of the biodegradable matrix.

In some embodiments, the growth factor is supplied in a liquid carrier (e.g., an aqueous buffered solution). Examples of aqueous buffered solutions include, but are not limited to, TE, HEPES (2-[4-(2-hydroxyethyl)-1-piperazinyl]ethanesulfonic acid), MES (2-morpholinoethanesulfonic acid), sodium acetate buffer, sodium citrate buffer, sodium phosphate buffer, a Tris buffer (e.g., Tris-HCL), phosphate buffered saline (PBS), sodium phosphate, potassium phosphate, sodium chloride, potassium chloride, glycerol, calcium chloride or a combination thereof. In various embodiments, the buffer concentration can be from about 1 mM to 100 mM. In some embodiments, the BMP-2 is provided in a vehicle (including a buffer) containing sucrose, glycine, L-glutamic acid, sodium chloride, and/or polysorbate 80.

Additional Therapeutic Agents

The growth factors of the present application may be disposed on or in the matrix with other therapeutic agents. For example, the growth factor may be disposed on or in the carrier by electrospraying, ionization spraying or impregnating, vibratory dispersion (including sonication), nozzle spraying, compressed-air-assisted spraying, brushing and/or pouring.

Examples of therapeutic agents include but are not limited to IL-1 inhibitors, such Kineret® (anakinra), which is a recombinant, non-glycosylated form of the human interleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as antioxidants, such as dilhiocarbamate, and other compounds, such as, for example, sulfasalazine.

Examples of therapeutic agents suitable for use also include, but are not limited to, an anti-inflammatory agent, analgesic agent, or osteoinductive growth factor or a combination thereof. Anti-inflammatory agents include, but are not limited to, apazone, celecoxib, diclofenac, diflunisal, enolic acids (piroxicam, meloxicam), etodolac, fenamates (mefenamic acid, meclofenamic acid), gold, ibuprofen, indomethacin, ketoprofen, ketorolac, nabumetone, naproxen, nimesulide, salicylates, sulfasalazine [2-hydroxy-5-[4-[C2-pyridinylamino)sulfonyl]azo]benzoic acid, sulindac, tepoxalin, and tolmetin; as well as antioxidants, such as dithiocarbamate, steroids, such as cortisol, cortisone, hydrocortisone, fludrocortisone, prednisone, prednisolone, methylprednisolone, triamcinolone, betamethasone, dexamethasone, beclomethadyl, fluticasone or a combination thereof.

Suitable analgesic agents include, but are not limited to, acetaminophen, bupivicaine, fluocinolone, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papavereturn, pentazocine, pethidine, phenoperidine, piritramide, dextropropoxyphene, remifentanil, tilidine, tramadol, codeine, dihydrocodeine, meptazinol, dezocine, eptazocine, flupirtine, amitriptyline, carbamazepine, gabapentin, pregabalin, or a combination thereof.

In some embodiments, a statin may be used. Statins include, but is not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastain (EP Appln. Publn. No. 738510 A2, the entire disclosure is herein incorporated by reference), eptastatin, pitavastatin, or pharmaceutically acceptable salts thereof or a combination thereof. In various embodiments, the statin may comprise mixtures of (+)R and (−)-S enantiomers of the statin. In various embodiments, the statin may comprise a 1:1 racemic mixture of the statin.

Kits

The matrix, growth factor and devices to administer the matrix may be sterilizable. In various embodiments, one or more components of the matrix, and/or medical device to administer it may be sterilizable by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In some embodiments, the matrix may be packaged in a moisture resistant package and then terminally sterilized by gamma irradiation. In use the surgeon removes the one or all components from the sterile package for use.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize the matrix and/or one or more components of the device, including, but not limited to, gas sterilization, such as, for example, with ethylene oxide or steam sterilization.

In various embodiments, a kit is provided comprising the growth factor, matrix, and/or diluents. The kit may include additional parts along with the matrix combined together to be used to implant the matrix (e.g., sponges, meshes etc.). The kit may include the matrix in a first compartment. The second compartment may include a vial holding the growth factor, diluent and any other instruments needed for the localized drug delivery. A third compartment may include gloves, drapes, wound dressings and other procedural supplies for maintaining sterility of the implanting process, as well as an instruction booklet. A fourth compartment may include additional needles and/or sutures. Each tool may be separately packaged in a plastic pouch that is radiation sterilized. A fifth compartment may include an agent for radiographic imaging. A cover of the kit may include illustrations of the implanting procedure and a clear plastic cover may be placed over the compartments to maintain sterility.

Figure 1:
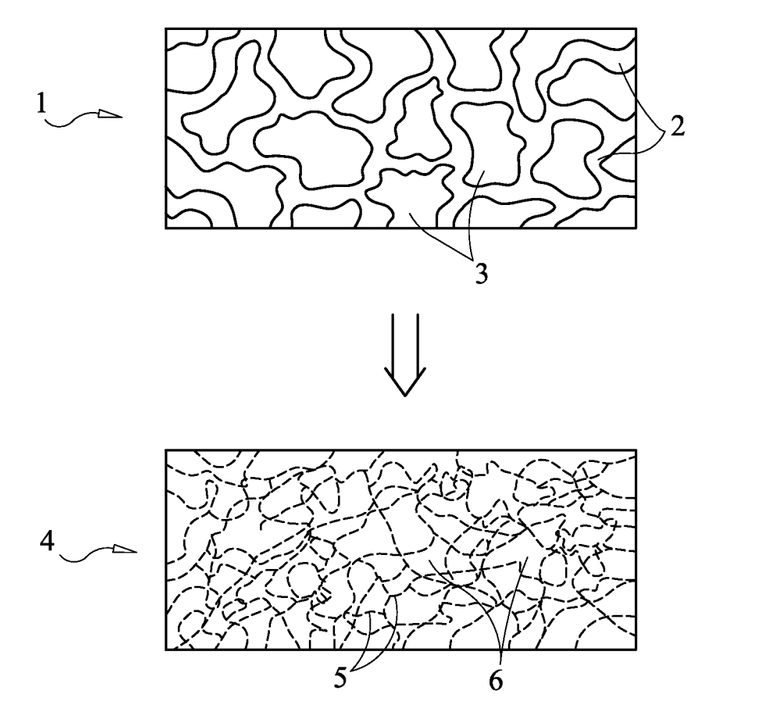
FIG. 1 is a representation of a ceramic skeleton of the present invention and a polymer matrix in which a ceramic skeleton is embedded.

The present invention may be further understood by reference to the accompanying FIGURE. FIG. 1 shows a ceramic skeleton 1. Both the skeletal portion 2 and the spaces 3 are shown. FIG. 1 also shows a polymer matrix in which the polymer has been added 4. The polymer 5 is shown as are the pores 6, which are smaller than the pores of the skeleton.

By way of a non-limiting example, the ceramic skeleton may have about 0.5 mm-3 mm thick struts (e.g., about 1.5 mm) and the polymer may have about 0.001-0.5 mm thick struts (e.g., about 0.01 mm). The matrix's gross dimensions may range from about 2-20 mm thick, about 5-40 mm wide, and about 10-60 mm long. The compression resistance may be about 2-40 MPa (e.g., about 5-20 MPa).

Compression resistance is needed for many tissue engineering applications such as tibial plateau fractures, acetabular defects, long bone comminuted fractures, oral maxillofacial defects, spinal fusions, and cartilage subchondral defects. Such a matrix will help facilitate adequate volumes of newly formed bone. At the time of surgery this composite structure can be cut by the surgeon to the desired shape to fit the tissue or bone defect and possibly hydrated with a bone inducing agent if necessary.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A compression resistant matrix for implantation at or near a target tissue site beneath the skin, the matrix comprising a porous ceramic skeleton disposed throughout the matrix in its interior and a polymer disposed throughout the matrix in its interior and extending to its exterior surface such that the matrix is porous and compression resistant, wherein the porous ceramic skeleton is interconnected with the matrix and is disposed continuously throughout the interior of the matrix and the polymer covers the porous ceramic skeleton, wherein the exterior surface of the matrix has a thickness of 0.01 to 1 mm, is seeded with harvested bone cells, and has a compression strength of about 2 MPa to about 40 MPa.

2. A matrix of claim 1, wherein the ceramic skeleton comprises a calcium phosphate ceramic material.

3. A matrix of claim 2, wherein the calcium phosphate ceramic material is tricalcium phosphate.

4. A matrix of claim 2, wherein the calcium phosphate ceramic material is amorphous hydroxyapatite.

5. A matrix of claim 1, wherein the polymer is collagen.
6. A matrix of claim 3, wherein the polymer is collagen.
7. A matrix of claim 4, wherein the polymer is collagen.
8. A matrix of claim 5, wherein the polymer is cross-linked.
9. A matrix of claim 5 further comprising a growth factor.
10. A matrix of claim 9, wherein the growth factor is rhBMP-2.
11. A matrix of claim 1, wherein said matrix is not compressed any more than about 10% in any one direction for a period of at least about 30 days in vivo.
12. A matrix of claim 11, wherein said matrix is not compressed any more than about 10% in any one direction for a period of at least about 60 days in vivo.
13. A matrix of claim 1 further comprising an analgesic agent.
14. A matrix of claim 5, wherein the ceramic skeleton has pores in the range of 1-10 mm in diameter, and a total porosity of 50-90%.
15. A matrix according to claim 14, wherein the collagen forms a matrix inside the ceramic skeleton that has pores in the range of 0.01-1 mm diameter and a total porosity of 80-99%.
16. A matrix of claim 1, wherein the matrix is seeded with harvested bone cells and bone tissue in a ratio of about 1:3 to 3:1.
17. A matrix of claim 16, wherein the bone cells and/or bone tissue comprises cortical bone, autogenous bone, allogenic bone, and/or xenogenic bone.
18. A matrix of claim 5, wherein the collagen comprises human collagen type I, human collagen type II, human collagen type III, human collagen type IV, human collagen type V, human collagen type VI and/or human collagen type VII.
19. A matrix of claim 1, wherein the matrix comprises about 0.2-2% collagen and about 98-99.8% ceramic.

* * * * *